(12) United States Patent
Punkka et al.

(10) Patent No.: US 8,292,820 B2
(45) Date of Patent: Oct. 23, 2012

(54) APPARATUS AND DEVICE FOR PERFORMANCE MONITORING

(75) Inventors: Eero Punkka, Helsinki (FI); Mikko Martikka, Vantaa (FI); Erik Lindman, Espoo (FI)

(73) Assignee: Suunto Oy, Vantaa (FI)

( * ) Notice: Subject to any disclaimer, the term of this patent is extended or adjusted under 35 U.S.C. 154(b) by 589 days.

(21) Appl. No.: 11/600,742

(22) Filed: Nov. 17, 2006

(65) Prior Publication Data

US 2008/0119329 A1 May 22, 2008

(51) Int. Cl.
- *A61B 3/12* (2006.01)
- *A61B 5/02* (2006.01)
- *A61B 5/08* (2006.01)
- *A61B 5/05* (2006.01)
- *A63B 71/00* (2006.01)

(52) U.S. Cl. ........ 600/484; 600/481; 600/483; 600/500; 600/503; 600/529; 600/531; 600/547; 482/8

(58) Field of Classification Search .......... 600/503, 600/500, 529, 534–536, 547, 484, 531; 482/8
See application file for complete search history.

(56) References Cited

U.S. PATENT DOCUMENTS

| | | | | |
|---|---|---|---|---|
| 3,994,284 A | * | 11/1976 | Voelker | 600/506 |
| 4,966,155 A | * | 10/1990 | Jackson | 600/484 |
| 5,316,008 A | * | 5/1994 | Suga et al. | 600/513 |
| 5,515,858 A | | 5/1996 | Myllymaki | |
| 5,795,301 A | | 8/1998 | Yasukawa et al. | |
| 5,810,722 A | * | 9/1998 | Heikkila | 600/300 |
| 6,282,439 B1 | | 8/2001 | Ruha | |
| 6,312,387 B1 | * | 11/2001 | Nissila et al. | 600/500 |
| 6,547,728 B1 | | 4/2003 | Cornuejols | |
| 6,982,930 B1 | | 1/2006 | Hung | |
| 2004/0030261 A1 | * | 2/2004 | Rantala | 600/561 |
| 2005/0049514 A1 | * | 3/2005 | Iwamiya et al. | 600/503 |
| 2005/0209521 A1 | * | 9/2005 | Kettunen et al. | 600/508 |
| 2006/0004265 A1 | * | 1/2006 | Pulkkinen et al. | 600/300 |
| 2006/0047208 A1 | | 3/2006 | Yoon | |
| 2006/0122521 A1 | * | 6/2006 | Chen | 600/503 |
| 2007/0265534 A1 | * | 11/2007 | Martikka et al. | 600/483 |

FOREIGN PATENT DOCUMENTS

CN 1751652 A 3/2006
(Continued)

OTHER PUBLICATIONS

"Use of EMFi as a Blood Pressure Pulse Transducer", Sorvoja et al., IEEE Transactions on Instrumentation and Measurement, vol. 54, No. 6, Dec. 2005.*

(Continued)

*Primary Examiner* — Patricia Mallari
(74) *Attorney, Agent, or Firm* — Birch, Stewart, Kolasch & Birch, LLP

(57) ABSTRACT

A method and wristop (wrist worn) device for monitoring physical exercise. The wristop device includes a central unit, in which there is a display face and to which a wristband is, or can be attached, sensor means for collecting a hemodynamic signal from the wrist, and a data-processing unit functionally connected to the sensor means, for deriving at least one physiological parameter from the hemodynamic signal. The data-processing unit of the wristop device is arranged to derive from the hemodynamic signal at least one physiological parameter depicting respiration, and further, on the basis of this, to calculate at least one training-effect parameter depending on the person and the exercise. In addition, the device makes it possible to eliminate the use of pulse bands in monitoring the training effect of exercise.

27 Claims, 3 Drawing Sheets

FOREIGN PATENT DOCUMENTS

Figure 1:
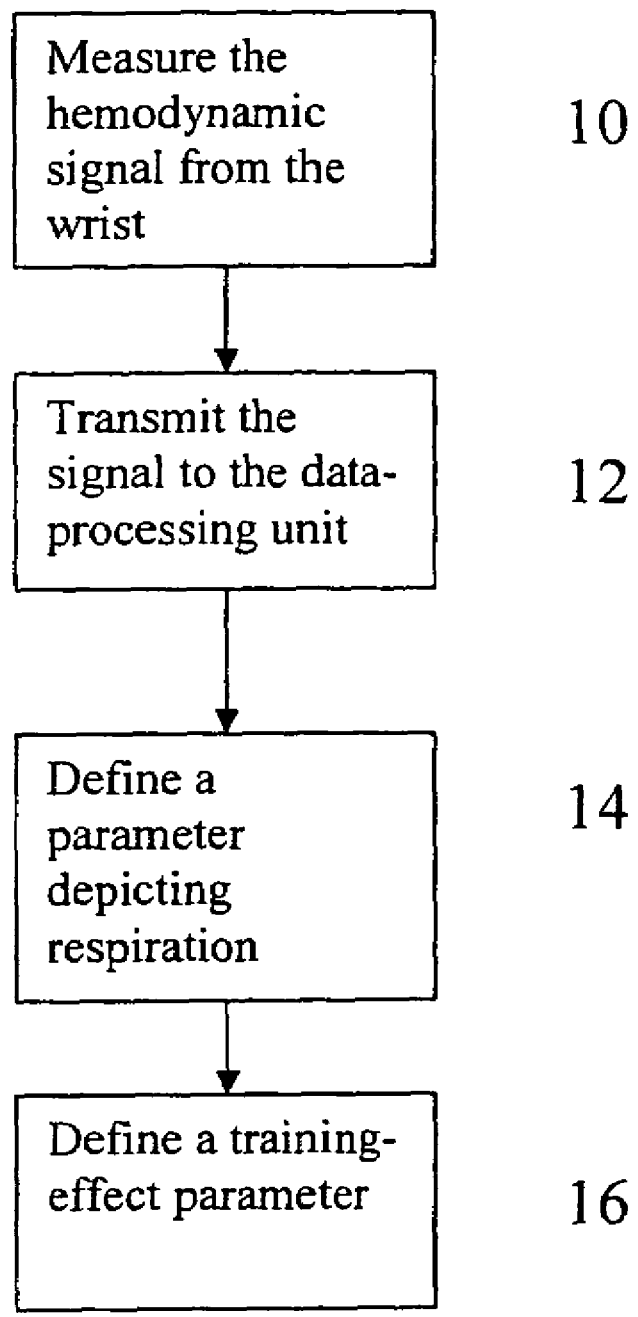

| | | |
|---|---|---|
| EP | 0 575 984 A2 | 12/1993 |
| EP | 1 034 736 A1 | 9/2000 |
| WO | WO 96/11630 * | 4/1996 |
| WO | WO 00/28892 * | 5/2000 |
| WO | WO-00/28892 A1 | 5/2000 |
| WO | WO-2005/032365 A1 | 4/2005 |

OTHER PUBLICATIONS

Sorojova et al., IEEE Transactions on Instruments and Measurement, vol. 54, No. 6, (Dec. 2005).

Farag Ph.D. et al., Biomedical and Instrumentation & Technology, pp. 311-314, (1994).

N. K. Kristiansen et al., Medical & Biological Engineering & Computing, vol. 43, pp. 516-521, (2005).

Firstbeat Technologies, Ltd., VO2 Estimation Method Based on Heart Rate Measurement, pp. 1-3, (2005).

Firstbeat Technologies, Ltd., EPOC Based Training Effect Assessment, pp. 1-5, (2005).

Firstbeat Technologies, Ltd., Indirect EPOC Prediction Method Based on Heart Rate Measurement, pp. 1-5, (2005).

* cited by examiner

APPARATUS AND DEVICE FOR PERFORMANCE MONITORING

The present invention relates to methods and devices, by means of which the exercise of persons can be monitored during the exercise. In particular, the invention relates to wristop devices, namely devices worn on a person's wrist.

A long-term objective in the heart-rate monitor sector has been to create measurement of heart rate that takes place directly from the wrist. Many methods have been developed to detect heart rate, the most important of which being capacitive 'listening' to the pulse, based on the use of an EMFi (Electromechanical Film), the monitoring of changes in the impedance or inductance of the blood (bio-impedance/bio-inductance) caused by the pulse, and mechanical detection of the pulse. Echo sounding of the pulse with the aid of ultrasound, and the reflection, dispersion, or absorption of light in the infrared range can be used to detect the pulse. In addition, acoustic listening to the pulse has been tried.

In the known methods and devices, a drawback is the poor signal quality and thus the poor reliability of the heart-rate data. The pulse sensors are typically located in the wristband of the device, because on the volar side (palmar side) of the wrist the closeness of the blood vessels means that both the electrical and mechanical pulse signals are stronger. However, even these signals are considerably more difficult to pick up than, for example, the electrical measurement of the QRS complex of the heart, which is implemented with the aid of two electrodes on the chest. As far as is known, there are no devices on the market that are able to successfully measure the heart rate particularly from the dorsal side of the wrist, i.e. from the side on which the central unit of the wristop device is typically worn.

Devices utilizing measurement on the volar side of the hand are disclosed in, for instance, WO publication 00/28892, US publication 2006/0047208, and the publication *Design and evaluation of a handheld impedance plethysmograph for measuring heart rate variability. Medical and Biological Engineering & Computing* 2005, Vol. 43. A pulse-electrode pair on the dorsal side of the wrist is referred to in US publication 2006/0122521.

Methods are also known (e.g., EP 0575984, U.S. Pat. No. 6,982,930), in which only half of the measurement takes place from the hand, so that the signal is measured between at least two limbs. In a wristop-device application, the user is required to be in contact with the electrode or electrodes of the wristop device from the other hand too, which is neither comfortable, nor necessarily even possible during exercise.

The resources of the sector have been continuously directed to developing an increasingly sensitive wrist sensor arrangement, which would allow the widely-used pulse belts placed around the chest and similar solutions to be abandoned in heart-rate monitoring during exercise. So far, however, pulse belts are unsurpassed in reliability. Reliable measurement of the heart rate has been generally regarded as being such an essential function, that consumer devices utilizing only wrist measurement are still not on the market.

Though wrist measurement technology has indeed been developed, it may be that in the near future it will not yet be possible to measure the heart rate reliably from the wrist, and perhaps never from the dorsal side of the wrist—at least during exercise when using an independent wristop computer carried by the exerciser, or using other similar devices.

The invention is intended to create a wristop device suitable for assessing the training effect, which exploits measurement of a hemodynamic signal, made from the wrist, in a new and reliable manner.

The invention is also intended to create a new method for assessing the training effect.

The invention is based on the observation that respiratory frequency, or other parameters relating to respiration can generally be detected even from such hemodynamic signals, from which the pulse rate cannot be determined. Respiratory frequency can, in turn, be applied directly to the calculation of energy consumption during exercise. Information on energy consumption is, for its part, sufficient to a large group of users and is, in fact, information that is even more interesting than an absolute heart-rate value. Thus, with the aid of the invention, it is possible to create a reliable method for assessing the training effect of exercise, as well as a device for this purpose, which can be manufactured economically and reliably.

In the method according to the invention, a person's physical performance is observed during exercise, in such a way that hemodynamic signals are collected by a sensor situated on the wrist and the hemodynamic signal is transmitted to a data-processing unit, in which at least one physiological parameter depicting respiration is derived from the signal. On the basis of this, at least one training-effect parameter depending on the person and the exercise is further calculated.

The device according to the invention, carried on the wrist, comprises a central unit, in which there is a display face and sensor means for collecting a hemodynamic signal from the wrist. In addition, there is, in the device, a data-processing unit connected functionally to the sensor means, which is arranged to derive at least one physiological parameter depicting respiration from the hemodynamic signal, and further, to calculate on the basis of this at least one training-effect parameter dependent on the person and the exercise.

More specifically, the method according to the invention is characterized by what is stated in the characterizing portion of Claim 1. The device according to the invention is, in turn, characterized by what is stated in the characterizing portion of Claim 16.

We have been surprised to observe that a sensor arrangement, particularly electrical electrodes or an electret membrane (such as an EMFi membrane), installed in the wristop device, even on the rear panel of the wristop device, can be used to collect a signal sufficient to determine the respiratory frequency and from that the energy consumption.

The weakness and poor quality of the signal have proved to be a problem, especially in the detection of pulse taking place from the wrist, nor has a good way of improving the signal been yet developed. When measuring the pulse from the chest, the heart's QRS complex is generally measured electrically, because this way has shown itself to be unsurpassed in reliability. However, the clear measurement of the QRS complex from a limb during exercise will not succeed. According to the present invention, by giving up the need to detect the heart rate and by detecting the respiratory frequency, it is possible, however, to obtain from even a poor-quality signal that which is often of the greatest interest to the user, i.e. the training effect. Thus, in order to implement the invention it is not essential for the pulse rate to be detected (or even for it to be possible to be detected) from the signal. However, in certain embodiments it is advantageous for at least some of the pulses to be detected, as will be explained later in greater detail.

According to the best-regarded embodiment of the invention, the hemodynamic signal is collected from the dorsal side of the wrist. In the corresponding device, there is a rear panel, opposite to the display face, in which the sensor means are situated. Even though, due to the more distant location of the large blood vessels, the strength of the signal is clearly weaker on the dorsal side than on the volar side, we have observed dorsal measurement to be, however, sufficient for the present purpose, i.e. the assessment of training effect on the basis of respiration.

At its most general, the invention is in no way restricted to the method of detecting a specific hemodynamic signal. In principle, any non-invasive method whatever, which is sensitive to the periodic changes in the blood vessels caused by respiration, is suitable for use in connection with the invention. However, by using some specific methods particular advantages can be achieved, for example, relating to the assembly, price, or power consumption of the device, or in relation to the range of sports in which the device can be used. For example, in swimming and running it may not necessarily be possible to use the same method to detect a hemodynamic signal. Measurement methods, which are more sensitive to the respiration component of the signal than to the pulse component, are especially advantageous when applied in the sphere of the invention.

Generally, considerable advantages relating to the manufacture of the device are gained with the aid of the invention. This is precisely because with its aid the use of pulse bands or a corresponding sensor arrangement can be avoided. In particular, placing the sensors on the rear panel of the device, against the dorsal side of the hand, will avoid the problems of sensors installed in the wristband and thus of manufacturing a contact between the wristop device's central unit and the wristband. As is known, it is difficult and expensive to make flexible and durable electrical contacts between the wristband and the device's central unit.

The invention is also advantageous from the point of view of the end user, as the user needs only one device to estimate the training effect of exercise. In the sector, a need for such new applications has existed for several years, as they make it as easy as possible for a user to start the exercise being assessed, which will further encourage the user to improve their condition and analyse their performance.

We use the term dorsal side of the wrist to refer to the surface located on the side of the back of the palm, defined by the large wrist bones.

Figure 2:
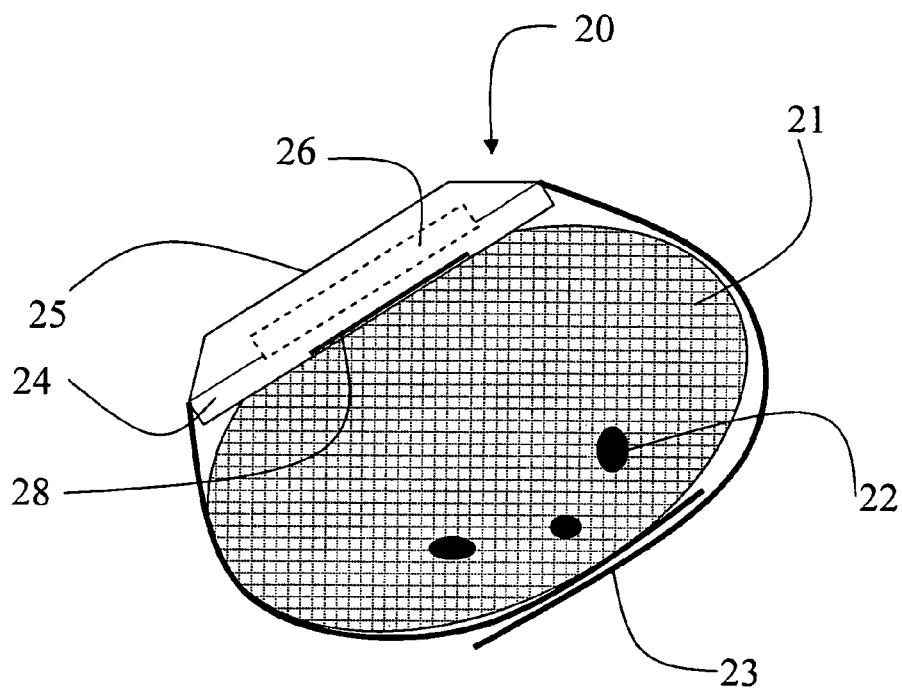
Figure 3:
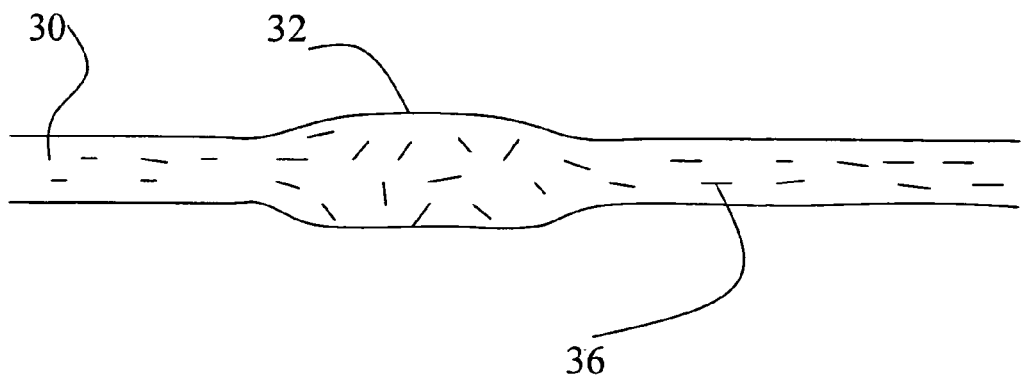
Figure 4:
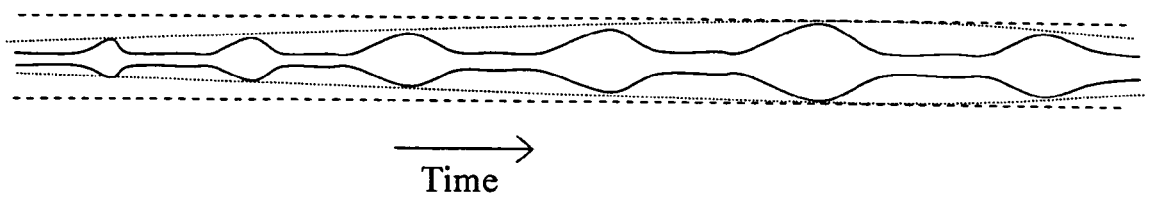

In the following, the invention is examined in greater detail with reference to the accompanying drawings, in which FIG. 1 shows a flow diagram of the method stages typical of the invention, FIG. 2 shows a schematic cross section of a training monitor worn on the wrist, FIG. 3 shows a schematic diagram of the behaviour of the blood cells during a pulse, and FIG. 4 shows a schematic diagram of the effect of respiration in modulating the amplitude of a pulse signal.

Each heartbeat causes a flow in the blood vessels and causes in turn a small bulge that moves in the direction of the vessel, which is shown by the reference number 32 in FIG. 3. On the basis of plethysmographic measurements, it is known that blood vessels expand temporally, not only due to the effect of the heartbeat, but also in time with respiration. Thus respiration changes the pressure in the circulatory system cyclically. This is because when breathing in, and thus when the chest muscles expand, the pressure in the blood vessels decreases, while in breathing out the opposite applies. The 'suction' created by respiration thus creates a change in pressure, which is well transmitted in a fluid, i.e. in this case in blood. In a healthy person, the pulse rate is many times greater than the respiration rate. Respiration thus appears as a lower-frequency modulation in the blood flow, i.e. as a change in the cyclic height of the pulses. This is illustrated in FIG. 4. According to the invention, this modulation is detected from the hemodynamic signal collected from the wrist, which we have shown to be more reliably picked out from a very high-noise signal.

Due to the non-spherical shape of blood cells 36 (mainly red cells), the degree of organization of the blood cells in a bulge 32 changes during a heartbeat. The change in degree of organization appears as a change in the electrical conductance (impedance) of the blood vessels and thus on the entire tissue. This property can be exploited in various embodiments, as will later be explained in greater detail. One example of a measurement system exploiting measurement from the volar side of the wrist is described in the article '*Detection of Pulse and Respiratory Signals from the Wrist Using Dry Electrodes,*' Farag et al, Biomedical Instrumentation and Technology, July/August 1994.

In FIG. 1, the signal collection is, marked with the reference number 10. The signal is transferred to the data-processing unit (processing unit) in stage 12. In the data-processing unit, the respiratory frequency is detected from the signal in stage 14. Some possible methods for achieving this are described below.

According to a preferred embodiment, the measured signal is low-pass filtered; so that the respiratory frequency can be calculated on the periodicity of the filtered signal, i.e. typically time data of the maxima (or minima). In this embodiment, detection or observation of the individual heartbeats is thus in no way essential, and is therefore typically not performed to measure the respiratory frequency.

Instead of respiration-frequency definition taking place in the time plane, definition that takes place in the frequency plane can also be used. In that case, the collected hemodynamic signal is converted to the frequency plane with the aid of a discrete Fourier transformation (DFT) and the respiration component is extracted from the converted signal. Known co-ordinate conversion, filtering, and/or pulse-detection techniques are among those that can be used generally in the signal processing.

In general, the frequency of the respiration modulation is detected from the hemodynamic signal most advantageously in a manner independent of the heart-rate modulation. Thus, also or only the signal collected from the signal periods between the heartbeats (heartbeat-interval periods) are used to determine the respiratory frequency. The embodiments described above come into this category.

It should be noted that, even though the invention does not require either the heartbeat density, or even the individual heartbeats to be detected from the signal, it is possible to monitor these too, or at least to attempt to monitor them, in order to create alternative or particularly advantageous embodiments. Particularly in the future, if it becomes possible to improve the sensitivity of the measurement methods, it may become possible to reliably detect individual heartbeats, or the heart rate from the dorsal side of the wrist. Some embodiments that would then permit this are described below.

According to one embodiment, in order to determine the respiratory frequency, individual heartbeats and further the height variations in the signal caused by them are detected. In turn, the frequency of the respiratory modulation is derived from the cycles of the height variations. This has the advantages, compared to known solutions, that even if individual heartbeats remain undetected, it is possible nevertheless to calculate the frequency of the lower-frequency respiratory modulation from the results. However, it is preferable if the detection of the heartbeats at a mean frequency, which is twice that of the respiratory frequency, is successful. However, this frequency can be considerably lower than the heart rate, at least half of it and even lower. By using the typical respiration and pulse frequencies, it is thus possible to determine the respiratory frequency, even though on average every second heartbeat remains undetected. According to one embodiment, a parameter depicting respiration is derived from a hemodynamic signal, even if the quality of the signal is insufficient for detecting a reliable heartbeat density.

According to one embodiment, the respiratory frequency is determined at least partly on the basis of the periodicity of the temporal variation (i.e. the so-called heartbeat interval noise) of the heart-rate data contained in the heart-rate signal. The period of the heartbeat interval noise can be calculated through a frequency conversion, or preferably directly in the time plane. In that case, typically a series comprising consecutive time points is created from the time stamps, the period of the series is determined, and the respiratory frequency is determined on the basis of the period of the series. The period of the series can be further determined by calculating the second derivative of the series and searching for its zero point. The advantage of a definition performed in the time place, compared to an analysis made through a frequency conversion is a reduced need for calculation. Thus the calculation is rapid and can be performed using a small processor and program-memory capacity, thus also reducing the current consumption and making the device more economical.

However, pulse-based respiration measurements always produce a small error when determining the respiratory frequency, so that it is more advantageous to use 'direct' methods independent of the pulse, as described above.

If the quality of the hemodynamic signal collected is sufficient to detect all the pulses, the heart rate is preferably determined from the signal in the time plane, with the aid of a discrete Fourier transformation (DFT).

In order to improve the reliability of the respiratory frequency, it may be advantageous to also detect the heart rate from the hemodynamic signal, or some variable that correlates with this, and then to compare this variable with the respiratory frequency. An example of an application, in which there is benefit in such a comparison, is detection of a stress situation. When the body reacts to stress, adrenalin enters the bloodstream and the heart rate increases. On the basis of the present state of knowledge, the increase in heart rate is due to the blood circulation being made to boost the transmission of adrenalin and thus to increase muscular readiness. The idea of measuring stress is based on this. According to a preferred embodiment, stress measurement based on the comparison of respiratory frequency and heart rate can be implemented utilizing the invention, in such a way that respiration and the noise in the measured signal, or a variable corresponding with the heart rate and calculated from the noise, or the actual heartbeat, are monitored. If the noise is determined to rise without an rise in the respiratory frequency, this can be decided to be some form of stress reaction. It should be noted, that in this embodiment too there is no need to know the absolute value of the heart rate, instead its relative value (such as the noise level of the signal, etc.) will be sufficient. In general, information of an unusually rapid change in the heart rate, derived from a hemodynamic signal, relative to the change in respiratory frequency will be a sufficient indication of a change in the stress state.

In some embodiments, previously provided data can be used as an aid in the calculation of respiratory frequency, for example, on the normal variations in heart rate and/or respiratory frequency, or of a typical correlation during exercise. In this way, it is possible to further improve the reliability of the method in a wristop environment.

Using the determined respiratory frequency, some training-effect parameter is, in turn, calculated in stage 16. We use the term training-effect parameter to refer to a variable depending on exercise and the exerciser, which depicts the degree of stress of the exercise, the energy consumption it causes, or some other effect on the physical state of the exerciser, their general condition, or their recovery. The most typical training-effect parameters used at momentary or cumulative energy consumption or EPOC (Excess Post-exercise Oxygen Consumption), or some variable further derived from these. Such a variable can be, for example, the 'Training Effect', which depicts the effect of improvement of condition, that is, aerobic performance.

EPOC depicts the amount of oxygen, which is needed, after an activity that stimulates the body through exercise, to return the body to its normal state, to homeostasis. According to one embodiment of the present invention, the EPOC accumulated during exercise is estimated at least partly on the basis of respiratory frequency, determined according to the invention. The exploitation of EPOC to direct training is described in great detail, for example, in US publication 2006/0004265 and in other publications of Firstbeat Technologies Oy (e.g., the white papers of May 2005 and September 2005).

According to one preferred embodiment, a parameter depicting respiration is used to calculated energy consumption during exercise. In that case, at least one preliminary data is used as an aid, either of the person who is the object of the measurement and/or of the sport they perform. Preliminary data can comprise data measured from the person, such as the $VO_2$max value. According to the preferred embodiment, however, data that can be determined on the basis of tests or data not directly connected to oxygen intake are used, which can include, for example, the activity class of the person, their weight, height, or sex, or information on the nature of the sport performed by the person. The term nature of the sport refers primarily to whether it is a sprint type or an endurance type sport. The activity class (typically on a scale 1-10) can, on the other hand, be determined without physical tests, for instance, on the basis of the number of exercise sessions by the person. Other person or sport-specific data can also be used. The energy consumption or other training effect is calculated on the basis of a parameter depicting the preliminary data used and the measured respiration. According to a particularly preferred embodiment, selected preliminary data are used as direct scaling factors or the respiratory parameter or parameters, which simplifies and accelerates the calculation. Different weighting values can be applied to different preliminary data in the calculation. The final result is converted advantageously into a momentary value of energy consumption (e.g., kcal/min). The cumulative energy consumption of the exercise can also be calculated. The consumption can also be stated as relative values.

Particularly the respiratory frequency at the start or end stages of exercise, or at other changes in the rhythm of the training, do not generally correlate directly with the energy consumption at the moment, or with other training effects. When a person starts an exercise session, their respiration does not immediately reach a level comparable with the momentary energy consumption. On the other hand, at the end of exercise, or during a break in it, the respiratory frequency will remain high, even through the physical stress is over. These factors can, however, be taken into account, by monitoring temporal changes in respiratory frequency, heart rate, or some other measurable variable depicting a change in the rhythm of the exercise. If a change of a predefined magnitude over a specific period of time is detected in such a variable, the respiratory frequency can be corrected by calculation towards a respiratory-frequency value that corresponds better with the real training effect. The real-time correction can take place, for example, by retaining the momentary respiratory-frequencies for the duration of the examination in a buffer memory, and comparing respiratory frequency received last with the previous values of the respiratory frequencies. One versed in the art will understand on the basis of the above, that a calculation achieving the desired effect can be implemented in different ways.

The correction of the training effect is preferably performed in a boosted manner. This means that the values of the energy consumption are corrected more, relative to the magnitude in the change in the variable depicting the change in the rhythm of the exercise. This will compensate, for example, for-the slow change in respiration or heart rate, relative to the momentary intensity of the exercise. The variable depicting the change in rhythm can, of course, also be, for example, information received from an acceleration sensor, in which case a boosted correction may not necessarily be required.

In the following, a wristop device, by means of which the aforementioned method stages can be performed, is described by way of example, with reference to FIG. 2.

The wristop device preferably comprises a central unit 20, in which there is a display face 25 and a rear panel on the opposite side to this. A wristband 23 is, or can be attached to the central unit. Sensor means 28 for collecting a hemodynamic signal from the wrist are located essentially in the rear panel 24, typically on its surface or partly embedded in it, in such a way that they can be brought into contact with the skin, when the device is put on. The wristop device also comprises a data-processing unit 26, functionally connected to the sensor means 28, in which a respiration parameter is derived from the hemodynamic signal, from which in the data-processing unit 26 is further derived at least one training-effect parameter dependent on the person and the exercise. An example of the calculation of the training-effect parameter will be described later in greater detail.

It is preferable to use a sensor arrangement 28, which comprises several, preferably four, electrical bio-impedance measurement electrodes. In the sensor arrangement in the four electrodes, there is typically a first pair of electrodes for feeding current to the wrist, and a second pair of electrodes for detecting the respiration-modulated bio-impedance in the wrist. Most preferably, the electrodes are arranged consecutively/adjacent to each other, in such a way that the electrode pair formed by the outermost electrodes feeds current to the tissue. Detection can be take place, for example, using an electrode arrangement corresponding to that disclosed in publication WO 00/28892, but applied to the rear panel of the wristop device.

Alternatively, sensor arrangements based on mechanical pulse detection of the pulse can be used as the sensor arrangement. An example of such are sensor arrangements based on EMFi membranes or similar electret membranes, mechanical-capacitive sensor arrangements, and mechanical sensor arrangements based on springs and gels and liquids. The advantage of an EMFi membrane is its good sensitivity and lightness.

In the sensor arrangement, it is also possible to use other known and as yet unknown sensor, including optical (especially infrared-range) sensor, ultrasound sensors, and acoustic sensors. An example of measurement implemented using infrared technology is the method disclosed in US publication 6080110 for measuring heart rate actively from the outer auditory canal, with the aid of reflections of infrared light. This principle can also be applied in measurement performed from the dorsal side of the wrist. It is also possible to use passive infrared-range detection, in which case the movement in tissue of light produced by some external light source is monitored.

The sensor can take up part of the area of the rear panel lying against the skin, or essentially fill it completely. It is generally preferable if the device's base lying against the wrist, particularly the sensor arrangement of the base, is raised relative to the other parts of the device (especially the peripheral parts of the clock case). In this way, it is ensured that, when attaching the device to the wrist with the aid of a wristband, the sensor arrangement is securely connected and is thus capable of reliably transmitting a signal.

The central unit of the wristop device is preferably manufactured to be relatively light, so that its rear panel will remain better on the skin during exercise, i.e. looseness is reduced. Once the desired training-effect parameter or parameters have been defined, the end result can be shown to the user on the display face in an analog or digital form. The data can also be stored in the device's memory for later analysis.

The sensor arrangement can also be contained entirely in the wristband of the wristop device, in which case the strength of the signal can then be improved to some extent. Electrical contacts must then be made between the wristband and the central unit. Depending of the type of sensor arrangement, this can also be dispersed, in such a way that part of it is in the rear panel of the central unit and part is in the wristband.

The examples of embodiments described above do not restrict the invention and can be combined and varied freely. The Claims must be interpreted in their full scope, taking into account the equivalence interpretation.

The invention claimed is:

1. A method for monitoring a person's physical exercise during the exercise, the method comprising:
   collecting a hemodynamic signal using a sensor,
   transmitting the hemodynamic signal to a data-processing unit, and
   deriving at least one physiological parameter from the signal by using the data-processing unit,
   wherein the sensor and the data-processing unit are located in a portable device worn on a wrist of the person, and
   wherein the at least one physiological parameter derived from the hemodynamic signal is a respiratory frequency, the method further comprising:
   detecting a frequency of a respiration modulation from the hemodynamic signal in order to determine the respiratory frequency, the frequency of a respiration modulation being detected using a low-pass filter to yield a filtered signal, and by investigating a period of the filtered signal in a manner independent of a heart-rate modulation, and
   calculating at least one training-effect parameter, dependent on the person and the exercise, based on the determined respiratory frequency.

2. The method according to claim 1, wherein the sensor used for collecting the hemodynamic signal is located on a dorsal side of the wrist.

3. The method according to claim 2, wherein the sensor comprises at least two bio-impedance measurement electrodes.

4. The method according to claim 1, wherein the sensor comprises an electrode pair for feeding current to the wrist, and an electrode pair for detecting the respiration-modulated bio-impedance of the wrist.

5. The method according to claim 1, wherein the sensor is an electret membrane for detecting the pressure of a skin surface of the person.

6. The method according to claim 1, wherein the respiratory frequency is derived from the hemodynamic signal even though a quality of the hemodynamic signal is insufficient for reliable detection of a heart rate.

7. The method according to claim 1, wherein the training-effect parameter is energy consumption, or a derivative of energy consumption.

8. The method according to claim 1, wherein the training-effect parameter is EPOC (excess post-exercise oxygen consumption), or a derivative excess post-exercise oxygen consumption.

9. The method according to claim 1, further comprising:
detecting the frequency of a pulse modulation, or a variable correlating to the pulse modulation, from the hemodynamic signal, in order to determine an absolute or a relative heart rate, and
comparing the absolute or the relative heart rate with the respiratory frequency.

10. The method according to claim 9, further comprising:
detecting temporal changes in the absolute or the relative heart rate, relative to the changes in the respiratory frequency, in order to assess a stress state of the person.

11. A method for monitoring a person's physical exercise during the exercise, the method comprising:
collecting a hemodynamic signal using a sensor,
transmitting the hemodynamic signal to a data-processing unit, and
deriving at least one physiological parameter from the signal by using the data-processing unit,
wherein the sensor and the data-processing unit are located in a portable device worn on a wrist of the person, and
wherein the at least one physiological parameter derived from the hemodynamic signal is a respiratory frequency, the method further comprising:
detecting a frequency of a respiration modulation from the hemodynamic signal in order to determine the respiratory frequency, the frequency of a respiration modulation being detected using a low-pass filter to yield a filtered signal, and by investigating a period of the filtered signal, and
calculating at least one training-effect parameter, dependent on the person and the exercise, based on the determined respiratory frequency,
detecting the frequency of a pulse modulation, or a variable correlating to the pulse modulation, from the hemodynamic signal, in order to determine an absolute or a relative heart rate, and
comparing the absolute or the relative heart rate with the respiratory frequency, and
detecting temporal changes in the absolute or the relative heart rate, relative to the changes in the respiratory frequency, in order to assess a stress state of the person.

12. A method for monitoring a person's physical exercise during the exercise, the method comprising:
collecting a hemodynamic signal using a sensor,
transmitting the hemodynamic signal to a data-processing unit, and
deriving at least one physiological parameter from the signal by using the data-processing unit,
wherein the sensor and the data-processing unit are located in a portable device worn on a wrist of the person, and
wherein the at least one physiological parameter derived from the hemodynamic signal is a respiratory frequency, the method further comprising:
detecting a frequency of a respiration modulation from the hemodynamic signal, in order to determine the respiratory frequency,
wherein the frequency of the respiration modulation is determined by detecting a period of a heartbeat interval noise, and
calculating at least one training-effect parameter, dependent on the person and the exercise, based on the respiratory frequency.

13. The method for monitoring a person's physical exercise during the exercise according to claim 12, further comprising:
detecting the heartbeat interval noise in a time plane.

14. The method for monitoring a person's physical exercise during the exercise according to claim 12, further comprising:
detecting the heartbeat interval noise by stamping heartbeat data,
forming a time series, and
finding a period of the time series.

15. A method for monitoring a person's physical exercise during the exercise, the method comprising:
collecting a hemodynamic signal using a sensor,
transmitting the hemodynamic signal to a data-processing unit, and
deriving at least one physiological parameter from the signal by using the data-processing unit,
wherein the sensor and the data-processing unit are located in a portable device worn on a wrist of the person, and
wherein the at least one physiological parameter derived from the hemodynamic signal is a respiratory frequency, the method further comprising:
detecting a frequency of a respiration modulation from the hemodynamic signal in order to determine the respiratory frequency, the frequency of a respiration modulation being detected using a low-pass filter to yield a filtered signal, and by investigating a period of the filtered signal, and
calculating at least one training-effect parameter, dependent on the person and the exercise, based on the determined respiratory frequency,
wherein the respiratory frequency is derived from the hemodynamic signal even though a quality of the hemodynamic signal is insufficient for reliable detection of a heart rate.

16. A device adapted to be worn on a wrist for monitoring a person's physical exercise during the exercise, comprising:
a central unit, in which there is a display face and to which a wristband is attachable,
sensor means for collecting a hemodynamic signal from the wrist, and
a data-processing unit functionally connected to the sensor means, for deriving at least one physiological parameter from the hemodynamic signal,
wherein the data-processing unit is arranged to derive from the hemodynamic signal a respiratory frequency,
wherein the data-processing unit is arranged to detect a frequency of a respiration modulation from the hemodynamic signal by detecting a period of a heart-rate interval noise, in order to determine the respiratory frequency,
and further, on the basis of the respiratory frequency, to calculate at least one training-effect parameter depending on the person and the exercise.

17. The device adapted to be worn on a wrist according to claim 16, wherein the sensor means are located on a rear panel of the device on an opposite side of a central unit of a display face of the device.

18. The device adapted to be worn on a wrist according to claim 16 or 17, wherein the sensor means comprise at least two bio-impedance measurement electrodes.

19. The device adapted to be worn on a wrist according to claim 16, wherein the sensor means comprise an electrode pair for feeding current to the wrist, and an electrode pair for detecting a heart-rate and respiration-modulated bio-impedance of the wrist.

20. The device adapted to be worn on a wrist according to claim 16, wherein the sensor means comprise an electret membrane for detecting pressure from a skin surface.

21. The device adapted to be worn on a wrist according to claim 16, wherein the data-processing unit is arranged to derive a parameter depicting respiration from the hemodynamic signal even though a quality of the signal is insufficient for reliable detection of a heart rate.

22. The device adapted to be worn on a wrist according to claim 16, wherein the data-processing unit is arranged to detect the frequency of the respiration modulation from the hemodynamic signal in a manner independent of a heart-rate modulation.

23. The device adapted to be worn on a wrist according to claim 22, wherein the data-processing unit is arranged to detect the frequency of the respiration modulation from the hemodynamic signal, by using a low-pass filter to yield a filtered signal, and detecting the period of the heart-rate interval noise using the filtered signal.

24. The device adapted to be worn on a wrist according to claim 16, wherein the data-processing unit is arranged to detect the frequency of a pulse modulation from the hemodynamic signal, in order to determine a heart rate and further to compare the heart rate and the respiratory frequency with each other.

25. The device adapted to be worn on a wrist according to claim 24, wherein the data-processing unit is arranged to detect temporal changes in an absolute or a relative heart rate relative to changes in the respiratory frequency and to further assess a stress state of the person based on the changes.

26. The device adapted to be worn on a wrist according to claim 16, wherein the training-effect parameter is energy consumption, or a derivative energy consumption.

27. The device adapted to be worn on a wrist according to claim 16, wherein the training-effect parameter is EPOC (excess post-exercise oxygen consumption), or a derivative excess exercise oxygen consumption.

* * * * *